United States Patent [19]

Bobb et al.

[11] Patent Number: 4,988,863
[45] Date of Patent: Jan. 29, 1991

[54] OPTICAL FIBER REFRACTOMETER LAUNCHING LIGHT AT A NON-ZERO LAUNCH ANGLE

[75] Inventors: Lloyd C. Bobb, Warminster; Howard D. Krumboltz, Chalfont, both of Pa.

[73] Assignee: The United States of America as represented by the Secretary of the Navy, Washington, D.C.

[21] Appl. No.: 460,436

[22] Filed: Jan. 3, 1990

[51] Int. Cl.$^5$ .............................................. H01J 5/16
[52] U.S. Cl. ................................ 250/227.25; 356/133
[58] Field of Search .................... 250/227.25, 573, 574, 250/576, 904; 356/128, 133, 136

[56] References Cited

U.S. PATENT DOCUMENTS

| | | | |
|---|---|---|---|
| 3,520,619 | 7/1970 | Ward | 356/133 |
| 4,564,292 | 1/1986 | Omet | 356/133 |
| 4,711,126 | 12/1987 | Houpt et al. | 356/133 |

FOREIGN PATENT DOCUMENTS

D147877  4/1981  Fed. Rep. of Germany ...... 356/133

Primary Examiner—David C. Nelms
Assistant Examiner—Stephone B. Allen
Attorney, Agent, or Firm—James V. Tura; James B. Bechtel; Susan E. Verona

[57] ABSTRACT

The index of refraction of a liquid is measured using an optical fiber refractometer having a light transmitting optical fiber by immersing a portion of the optical fiber in the liquid and launching light into one end of the optical fiber at a selected non-zero launch angle with respect to the fiber axis. Light transmitted through the optical fiber is detected at the other end of the optical fiber and a determination is made of the index of refraction of the liquid in accordance with the detected light and the selected non-zero launch angle. By varying the launching angles of the light the range of the refractometer is increased. The light transmitting optical fiber is provided with a region having at least one tapered portion for further increasing the range of the refractometer. The tapered portion of the optical fiber is disposed between a refractive end of the optical fiber and the light source for providing single-ended operation.

6 Claims, 5 Drawing Sheets

OPTICAL FIBER REFRACTOMETER LAUNCHING LIGHT AT A NON-ZERO LAUNCH ANGLE

STATEMENT OF GOVERNMENT INTEREST

The invention described herein may be used by and for the Government of the United States of America for governmental purposes without the payment of any royalties thereon or therefor.

BACKGROUND OF THE INVENTION

This invention relates to optical refractometers and in particular to an optical fiber refractometer in which light transmission through an immersed fiber indicates refractive index.

The index of refraction of a liquid may be determined by filling a prismatic cell with the liquid of interest and by transmitting a collimated beam of light through the filled cell. The light transmitted through the cell is measured and the deviation of the beam due to refraction is determined. This method requires cumbersome optical instrumentation, manual adjustments, calculations, and handling of the liquid. It also requires liquid volumes in excess of one cubic centimeter.

Thus, methods using fiber optics were developed to permit the measurement of the index of refraction of liquids with a smaller volume of liquid. A basic fiber optic device for measuring the index of refraction of a liquid is taught in Canadian Pat. No. 1,184,780, issued to Jacques P. Legendre, entitled "Apparatus for Monitoring Refractive Index Changes in Fluids." In the apparatus taught by Legendre, an optical fiber was illuminated at one end while the other end was in contact with the fluid whose refractive index was to be measured. The optical energy reflected back from the interface between the end of the fiber and the liquid depended on the relative values of the refractive index of the liquid and the refractive index of the fiber. A signal was generated corresponding to the reflected energy and an electrical signal was generated corresponding to the energy provided by the optical source. From these measurements, the refractive index of the liquid was calculated.

Japanese Patent Application No. 59-97046, entitled "Device for Determination of Refractive Index of Fluid", disclosed a device wherein a curved light transmissible object was immersed in the liquid to be monitored. Light striking the walls of the light transmissible object due to the curvature of the object was partially reflected and partially refracted depending on the relative index of refraction of the light transmissible object and the liquid. The light travelled through the light transmissible object and was reflected from a reflecting section at the end of the object back to a photosensitive device. The amount of returning light was a measure of the refractive index of the liquid. However, such a device still required a relatively large volume of liquid since it was necessary to immerse the curved portion of the light transmissible object in the liquid.

U.S. Pat. No. 4,564,292, issued to Omet, disclosed a device requiring less liquid in order to make a measurement. In the device of Omet, a refractometer was provided on the tip of a measuring probe. The refractometer included a curved portion of a light conducting medium to permit measurement of a small amount of liquid by immersing the tip in the liquid to be measured.

A fiber optic refractometer using a tapered optical fiber is taught in "Novel Refractometer Using a Tapered Optical Fibre", by A. Kumar, in Electrical Letters, June 21, 1984, Volume 20, No. 13, page 534. The refractometer taught by Kumar is provided with an optical fiber adapted for immersion in the liquid being measured. One portion of the optical fiber had one diameter and a second portion of the optical fiber had a second diameter. A tapered region was provided between the two portions having different diameters. Light was transmitted from the larger diameter portion through the tapered region to the smaller diameter portion. The amount of light energy applied to the smaller fiber through the tapered region is related to the relationship between the indices of refraction of the optical fiber and the liquid in which the optical fiber is immersed. However, the optical fiber refractometer taught by Kumar was still limited in the range of indices it could measure from about n=1.33 to n=1.44.

SUMMARY OF THE INVENTION

The index of refraction of a liquid is measured using an optical fiber refractometer having a light transmitting optical fiber by immersing a portion of the optical fiber in the liquid and launching light into one end of the optical fiber at a selected non-zero launch angle with respect to the fiber axis. Light transmitted through the optical fiber is detected at another optical fiber end and a determination is made of the index of refraction of the liquid in accordance with the detected light and the selected non-zero launch angle.

DETAILED DESCRIPTION OF THE INVENTION

Figure 1:
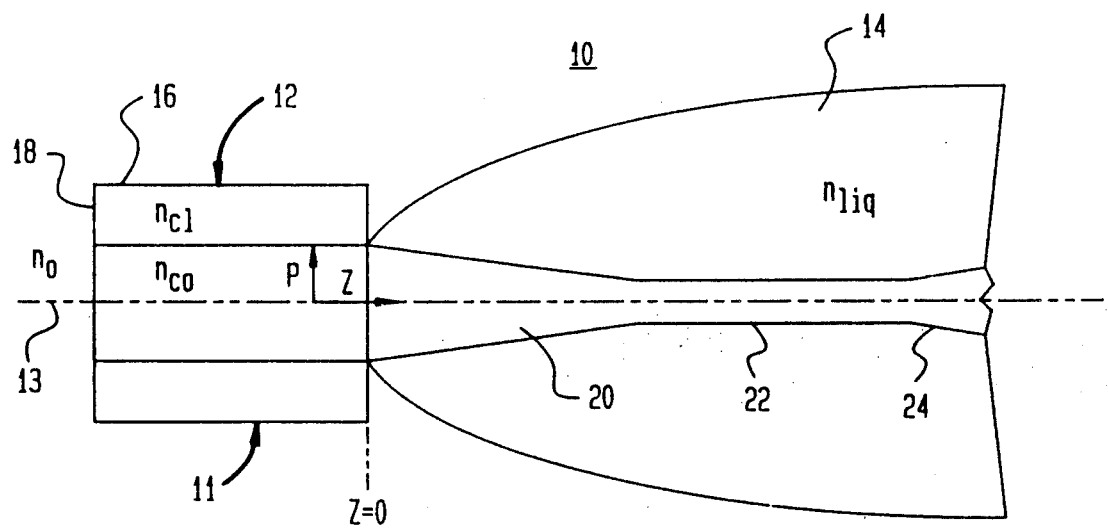
FIG. 1 shows the optical fiber refractometer system of the present invention comprising a tapered optical fiber with a portion of the cladding removed.

Referring again to FIG. 1, a more detailed description of the operation of optical fiber refractometer system 10 is provided. In optical fiber refractometer system 10 optical fiber 11 is immersed in liquid 14 which may have a range of values of indices of refraction. In refractometer system 10, both collimated and divergent light may be used, and, both the total intensity transmitted and the angular dependence are recorded. Because of the adjustment of the launch angle with respect to axis 13 of fiber 11 indices of refraction over the range of approximately 1.33 to approximately 1.62 may be determined.

The index of refraction of core 12 and cladding 16 are $n_{co}$ and $n_{cl}$ respectively and the radius of core 12 is $\rho(z)$. The angle $\theta_z(z)$ of a ray with respect to axis 13 of core 12 at the position z is related to the initial angle of the ray $\theta_z(o)$ at $z=0$ by the relationship $$\rho(z) \sin \theta_z(z) = \rho(o) \sin \theta_z(o). \quad (1)$$

We can see from Eq. (1) that $\theta_z(z)$ increases as $\rho(z)$ decreases. Therefore, a ray which is initially bound will become leaky if the radius of core 12 decreases below a certain value. Tapered region 20, then, increases the angular distribution of the light thereby increasing the range of refractometer system 10; and, the fraction of the power which exceeds the complement of the critical angle is lost from core 12. If a diffuse source (not shown) is used, the total bound-ray power in step-indexed optical fiber refractometer system 10 is.

$$P_{br} = I_o \frac{\pi^2}{n_o^2} (n_{co}^2 - n_{cl}^2) \rho^2 \quad (2)$$

where $I_o$ is the intensity per unit area of the source and $n_o$ is the index of refraction of the medium outside the endface of core 12. It can be shown that the fraction of the power emitted from narrow region 22 is $$f_p = \frac{P_{br}(22)}{P_{br}(18)} = \frac{\{n_{co}^2 - n_{liq}^2\} \rho^2(22)}{\{n_{co}^2 - n_{cl}^2\} \rho^2(18)} \quad (3)$$

where the cladding index of refraction $n_{cl}$ has been replaced by the liquid index of refraction $n_{liq}$. From Eqn. (3), it can be seen that for a given tapered fiber, $f_p$ decreases as the square of the index of refraction of the liquid surrounding narrow region 22.

Step-indexed optical fiber 11 may be formed of glass with the following nominal characteristics: $n_{co}=1.60$, $n_{cl}=1.48$, $d_{co}=68$ microns, $d_{cl}=75$ microns, and the NA=0.6. For example, fiber 11 may be a General Fiber Optics GL-75. Optical fiber 11 is cleaved and the ends are polished with less than four interference fringes across the face. This corresponds to height variations of less than 1.1 microns and a tilt of less than one degree. Fiber 11 is mounted along the axis of a 1.9 cm long×1.3 cm diameter nichrome heater and three to four grams of tension are applied. The change in the length of fiber 11 is monitored with a micrometer and a position locator which is temporarily fixed to fiber 11. Typical elongations of 11 are approximately one-half centimeter. This results in a tapered region 20 with a factor of three reduction in core 12 diameter between tapered regions 20, 24. The diameter profile of fiber 11 can be measured with a Gaertner microscope with a high precision translation stage. A one percent hydrochloric acid solution is used to etch tapered regions 20, 24 of optical fiber 11. A red LED (not shown) may be used with index matching gel to illuminate fiber 11, and, a silicon photodiode was used to measure the light intensity transmitted through tapered section 20 of the fiber 11 which was immersed in various refractive index liquids 14.

Figure 2A:
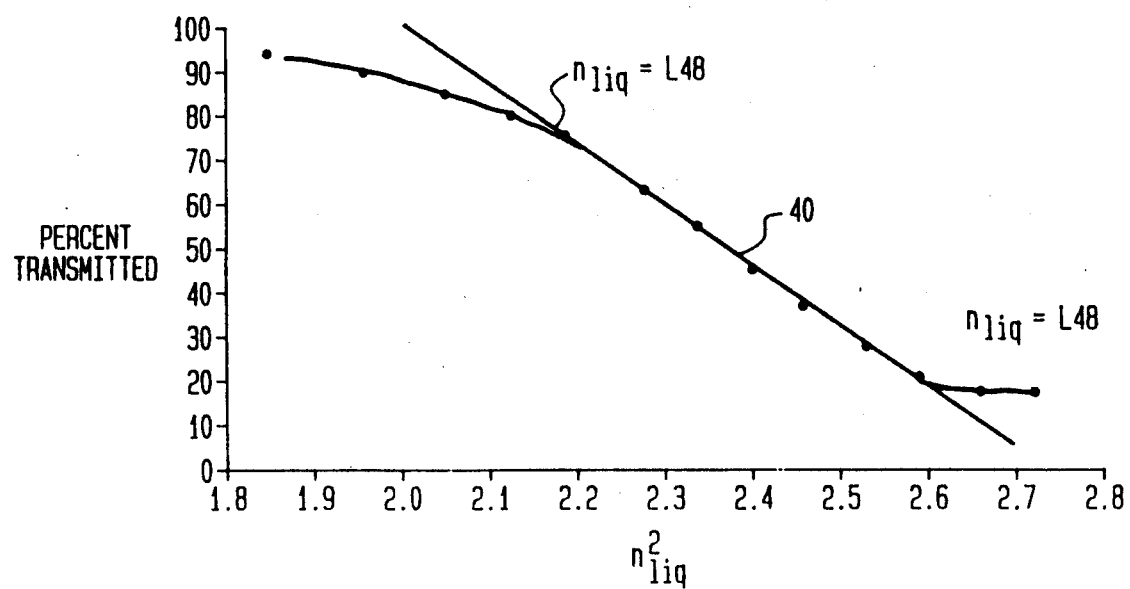
FIGS. 2a, 2b are graphical representations of the percent of light transmitted versus the square of the index of refraction for the liquid being measured using the optical fiber refractometer system of FIG. 1, wherein the optical fiber was not filled with light and a lens was used to fill the fiber with light, respectively.
Figure 2B:
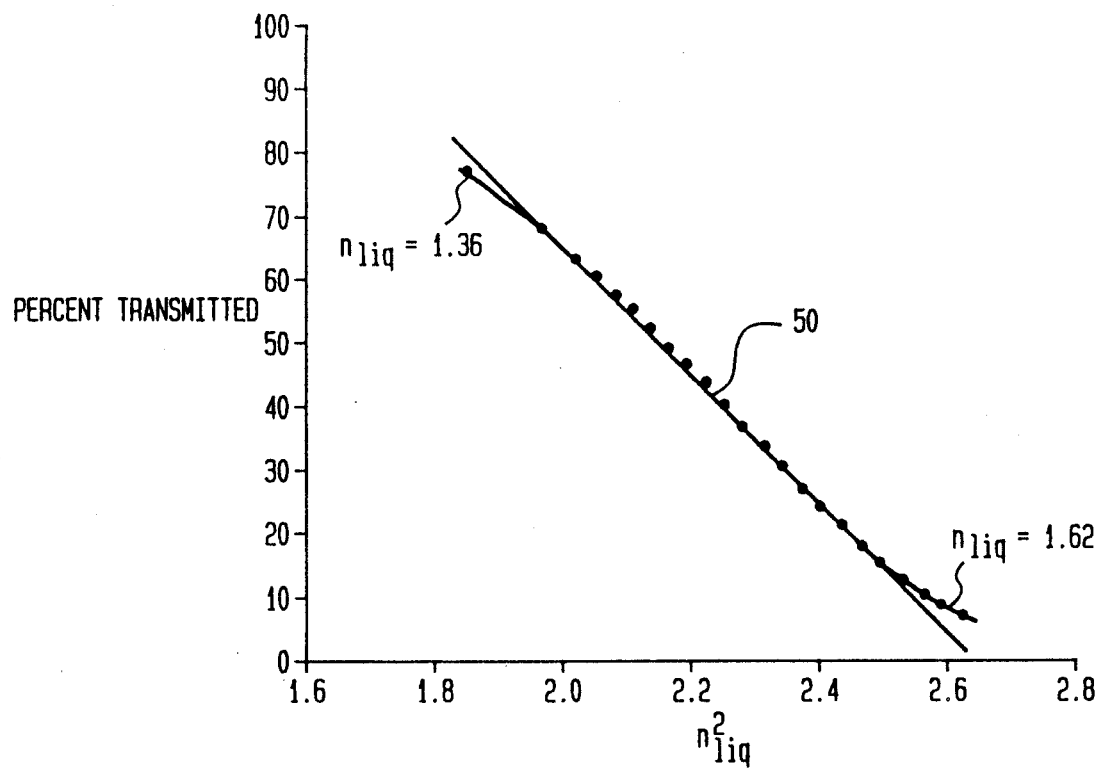
Figure 3:
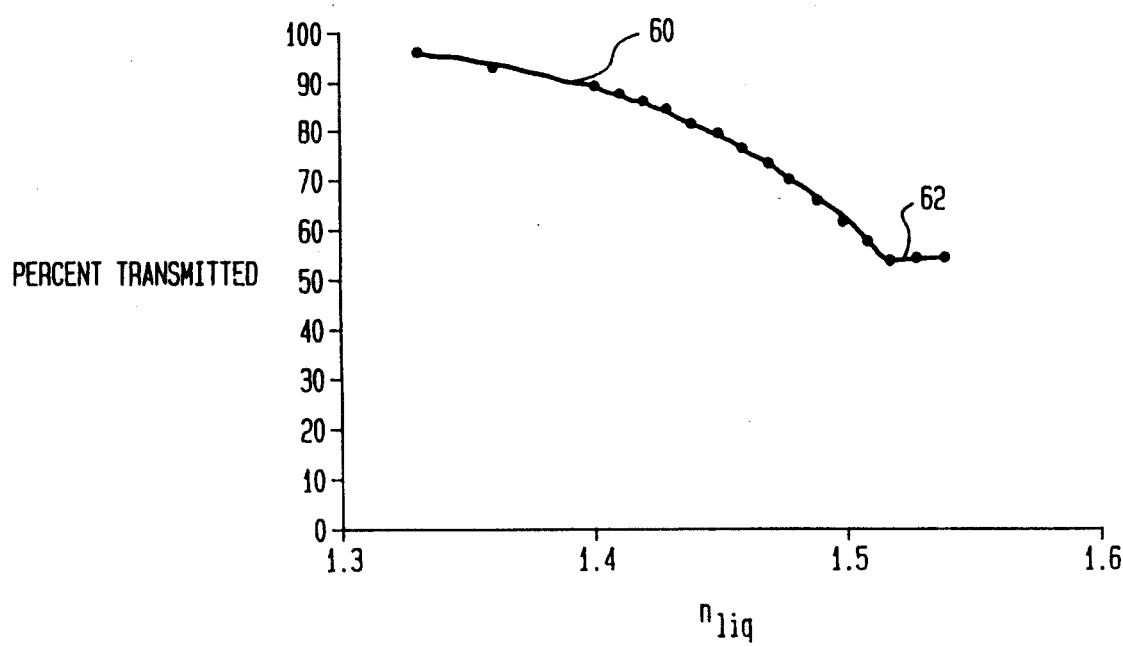
FIG. 3 is a graphical representation of the percent of light transmitted versus the index of a refraction of the liquid being monitored by the system of FIG. 1 using a tapered optical fiber which was not etched.

Referring now to FIGS 2a and 2b there are shown curves 40, 50, respectively, which are representative of the percent transmitted through core 12 versus the index of refraction of liquid 14 squared. FIG. 3 shows curve 60 which is representative of the percent transmitted through core 12 versus the index of refraction to the first power. This data was obtained with optical fiber 11 stretched one-half centimeter and lightly etched in one percent hydrochloric acid solution. The data points are normalized to one hundred percent transmission for air. Various transmission curves may be obtained depending on the amount of stretching the etching time. For example, curve 60 is representative of a tapered fiber 12 with light etching. Plateau 62 of curve 60 is a typical feature of unetched tapered fiber 11.

Figure 4:
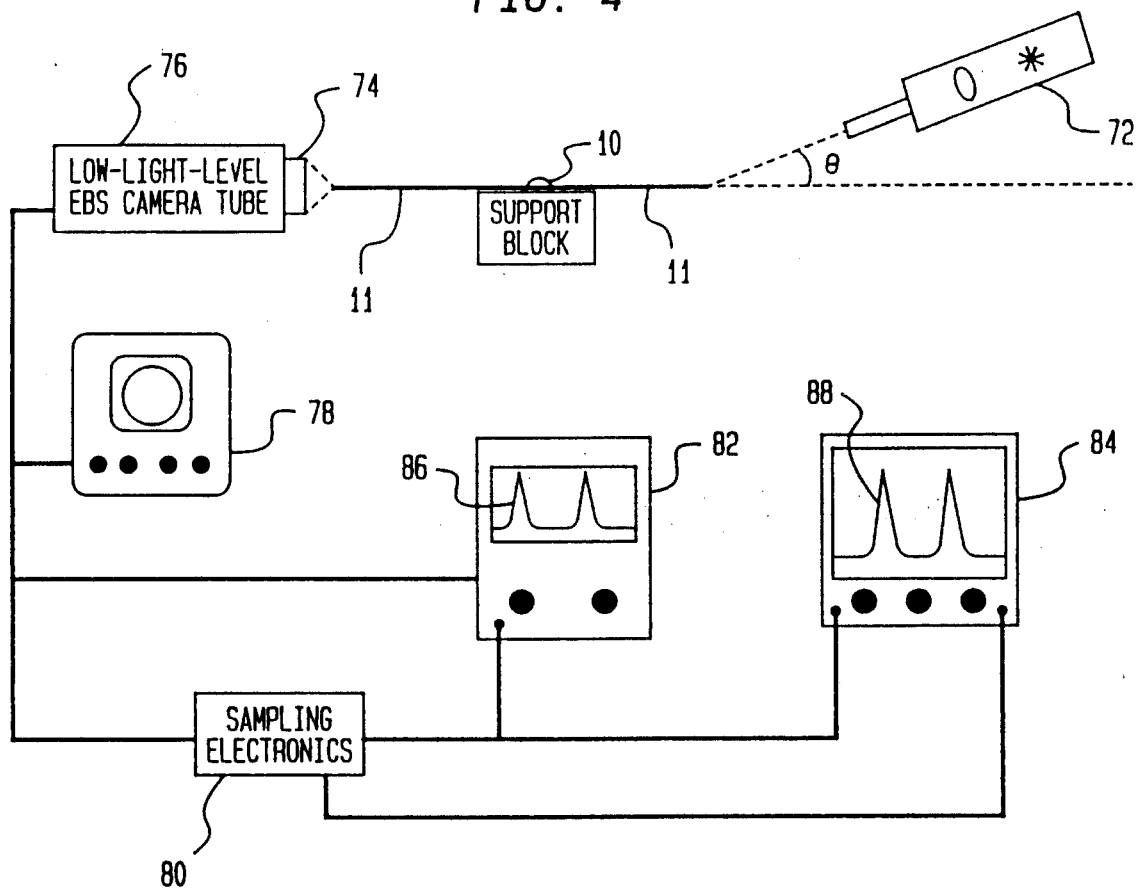
FIG. 4 shows the experimental arrangement used to launch various groups of modes in the optical fiber refractometer system of FIG. 1 and to image and record the modal distribution.

Referring now to FIG. 4, there is shown the experimental arrangement 70 for determining the effect of the taper of tapered region 20 and the index of refraction of fluid 14 on the various modes. One end of fiber 11 is held stationary at the center of a calibrated disc on which collimated light source 72 is mounted. The other end of optical fiber 11 is held a predetermined distance from face plate 74 of a low light level camera tube 76. The output of tube 76 is displayed on video monitor 78. Sampling electronics 80 are used to display and record a single line 86 of video on oscilloscope 82 or X-Y recorder 84. Line 86 is adjustable in order that the intensity profile across the center of the pattern may be displayed.

Figure 5:
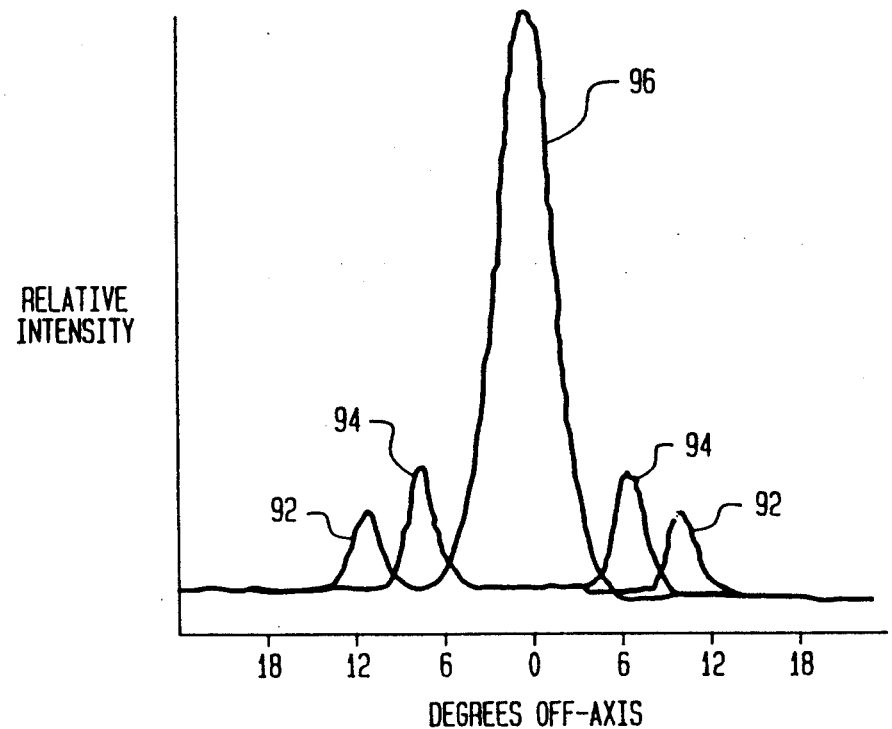
FIG. 5 shows a graphical representation of the relative intensity of the emitted light for light launched at plurality of angles into an unstretched optical fiber.

Referring now to FIG. 5, traces 92, 94, 96 are displayed for collimated light launched from light source 72 at zero degrees, seven degrees and eleven degrees with respect to fiber axis 13. These launch conditions result in a hollow cone of light being emitted from optical fiber 11 with the cone angle corresponding to the launch angle. This emitted cone of light forms a ring on face plate 74 of camera tube 76 which is calibrated in degrees. Thus, the ring diameter or the cone angle can be determined in degrees. Therefore, both incident and emitted light directions with respect to optical fiber axis 13 may be measured. Double peaked traces 92, 94 are sections through the rings along a diameter.

Figure 6:
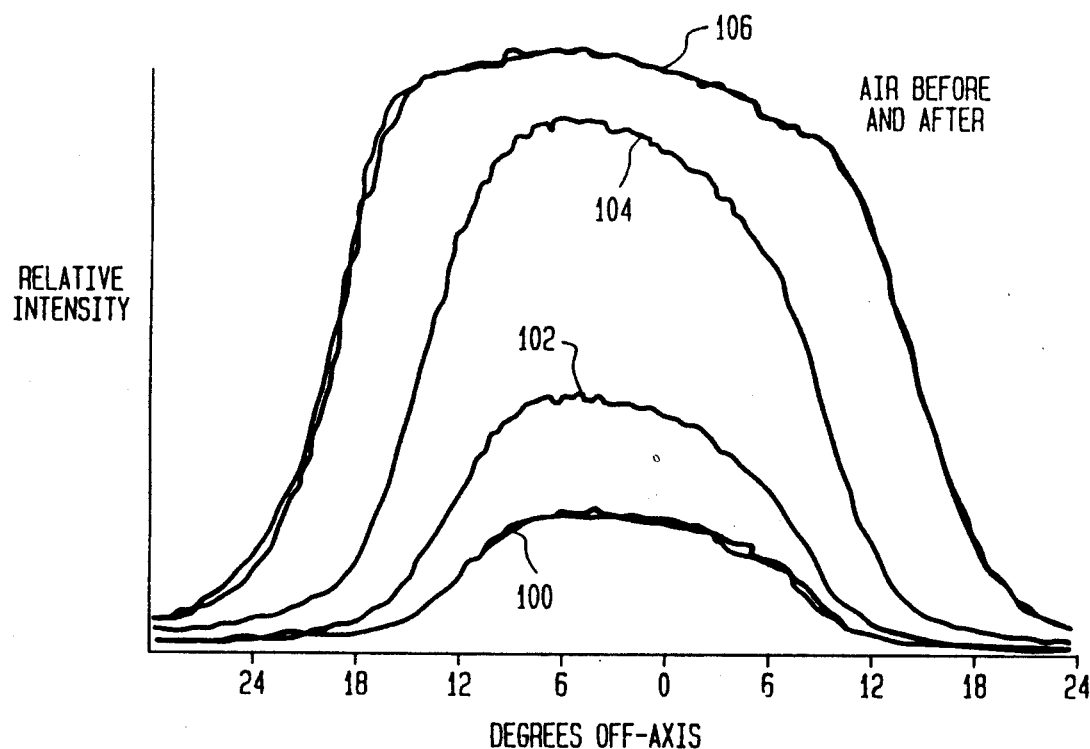
FIG. 6 shows a graphical representation of the relative intensity of light transmitted from the optical fiber refractometer system of FIG. 1 versus angle for different index liquids surrounding the tapered and etched region.

Referring now to FIG. 6, traces 100, 102, 104, 106 are shown. In addition to launching collimated light and imaging the emitted light, illumination for fiber 11 may be provided with an LED (not shown) closely coupled via an index matching gel and the light intensity versus angle may be recorded. Traces 100 correspond to liquids 14 with indices of refraction of 1.600 and 1.620. Trace 102 corresponds to a liquid 14 having an index of refraction of 1.520. Trace 104 corresponds to a liquid 14 having an index of refraction of 1.400. Traces 106, for air, were taken before and after the refractive index liquids 14 were used.

As represented by curve 40, the percent of the light transmitted through fiber 11 versus the square of the refractive index of liquid 14 is shown for refractive indices from 1.36 to 1.65. The data fit a straight line for refractive indices in the range 1.48 to 1.61. This agrees well with the model over the range bounded by the cladding and the core refractive indices. For this case, the deviation from linearity at lower index values arises from the light intensity distribution in fiber 11. The data of curve 50 were taken using the same optical fiber 11 as in the case of curve 40. However, when determining the data of curve 50 a lens (not shown) was used to fill fiber 11 with light. This extends the range of linearity to lower refractive index values. Other data on tapered fibers 11 cannot be fit to a straight line. The shape of the transmission versus $n_{liq}$ or $n^2_{liq}$ curve depends on the amount of stretching of fiber 11 and the amount of cladding 16 removed.

Curve 60 is a transmission versus index of refraction curve for a fiber 11 which was stretched 0.53 cm and not etched. In this case, the transmission decreases as the index increases up to n=1.52. Above this value the transmission levels off. The onset for plateau 62 goes to higher index values as the cladding is thinned by either etching or stretching. This behavior is in very good agreement with the predictions of the numerical model which depends on bounded rays tunneling through cladding layer 16 which is on the order of a wavelength thick.

The sensitivity of the stretched and etched multimode fiber 11 transmission to changes in the index of refraction of liquid 14 was determined by immersing tapered region 20 in a refractive index liquid with an index of refraction of 1.5150 and a temperature coefficient of $-0.00033/°C$. Refractive index liquid 16 was contained within copper block 71. The temperature of copper block 71 was slowly changed from the ambient. A thermocouple (not shown) was immersed in liquid 14 and a plot of the transmitted intensity versus temperature was made. The noise in the intensity measurement was less than the signal change associated with 0.1 degree change in the refractive index liquid. Conservatively, changes in index of refraction of $6 \times 10^{-5}$ are measurable. The dn/dt contribution from the glass was negligible.

To study the effects of the taper of region 20, the etching of cladding 16, and the refractive index liquids on the transmission properties of fiber 11, experiments were performed where groups of modes or light angles were launched and detected using imaging system 70. The data of curves 92, 94, 96 are from launching collimated light on-axis 13 and off-axis 13 into fiber 11 before stretching fiber 11. When fiber 11 is stretched, the individual peaks broaden slightly but remain in the same angular position. This would indicate that the modification of the angle according to Eqn. 1 in going from the larger radius to the smaller is offset by the reverse taper. The effect of a single taper was examined by cleaving a stretched fiber 11 between tapers and measuring the light deviation from axis 13 of fiber 11 for various launch conditions. The results were consistent with Eq. 1.

The off-axis modes are more sensitive than the axial modes to the changes in refractive index for lower index values. Therefore, the sensitivity of optical fiber refractometer system 10 can be improved for n=1.3 to 1.5 by launching modes which are radiated for cladding 16 index values in this range. This can also be seen by comparing traces 104, 106 representing experiments wherein fiber 11 is nearly filled with light. The difference between the air curves 106 (n=1.0) and the n=1.40 curve 104 increases as the ray angle increases. The data of curves 100, 102, 104, 106 were obtained from an optical fiber 11 which was stretched 0.60 cm and etched for two minutes in the previously mentioned solution. An interesting feature is that the higher order modes radiate for lower refractive index values, of the test liquid 14, and the lower order modes radiate when the index of refraction of the test liquid 14 is in the range 1.40 to 1.60.

Before etching, similar behavior was observed with the exception that the lowest throughput value was obtained for n=1.52 instead of 1.60. For other fibers 11 which are stretched and not etched, it is often observed that the light intensity in the zero to eight degrees range is unaffected by the refractive index liquids and only the higher order modes radiate. For these fibers 11, thinning cladding 16 by etching always decreases the near axial intensity with increasing index of refraction.

Tapered and etched multimode optical fiber 11 (GL-75) thus provides a highly sensitive refractometer system 10 over the range 1.33 to 1.60. The sensitivity of system 10 may be adjusted by stretching and etching fiber 11 and by launching and detecting different groups of modes in fiber 11.

Figure 7:
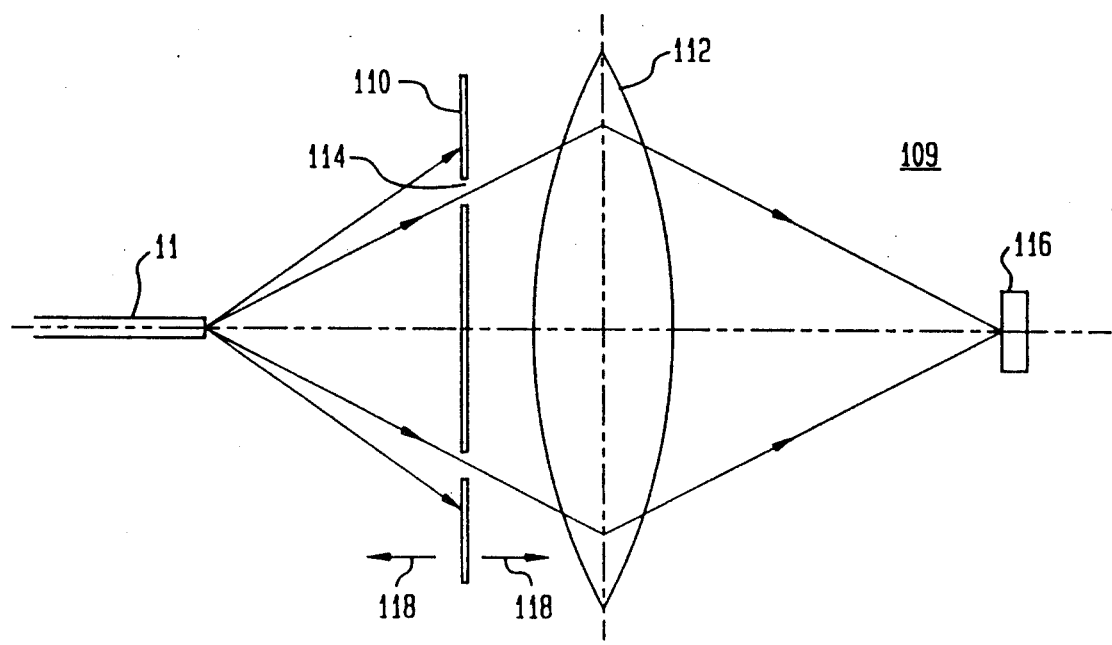
FIG. 7 shows a system for limiting the angle over which light is collected in the system of FIG. 4, and FIGS. 8a, 8b show an alternate embodiment of the system of FIG. 1.

Referring now to FIG. 7, there is shown system 109 for limiting the angles over which light is collected. Light from optical fiber 11 strikes translatable circular aperture device 110 having circular aperture 114. Translatable circular aperture 110 may be translated in the directions indicated by arrows 118. When translatable circular aperture device 110 is translated, light passing through circular aperture 114 from optical fiber 11 strikes lens 112 at varying angles. Light entering lens 112 is then transmitted to detector 116 at an angle dependent on the translated position of translatable circular aperture device 110.

The differences between the air curve and the n=1.400 curve of FIG. 6 is larger at fifteen degrees than at zero degrees. By selectively launching or collecting light at fifteen degrees, refractometer system 10 is made more sensitive for low index values. The other consideration here is that when measuring energy, the energy is in a ring of light where the angles in FIG. 6 represent the ring diameter. The effect of small changes in intensity at large angles is magnified because these small changes are integrated over the entire ring. Thus the system of FIG. 7 is useful for limiting the angles over which the light is collected. By translating device 10, different ring diameters or angles can be selected.

Figure 8A:
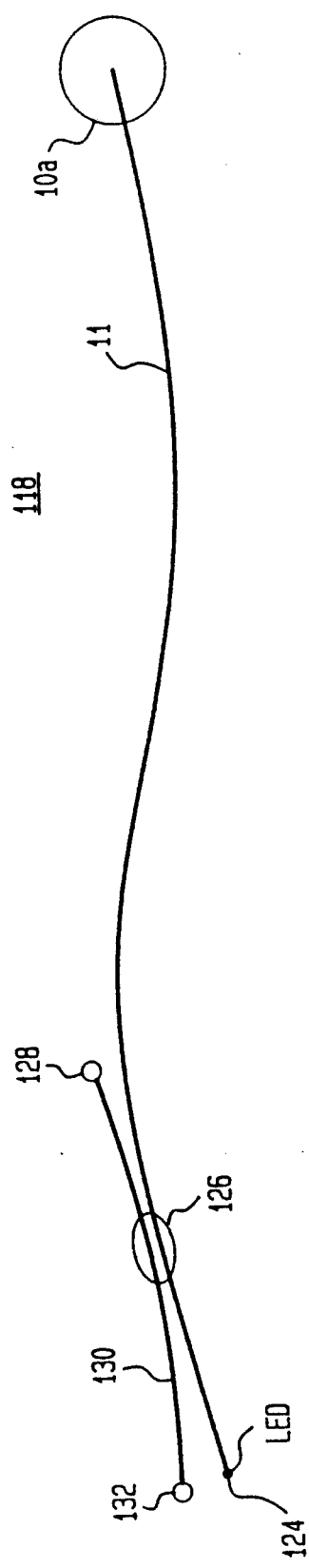
Figure 8B:
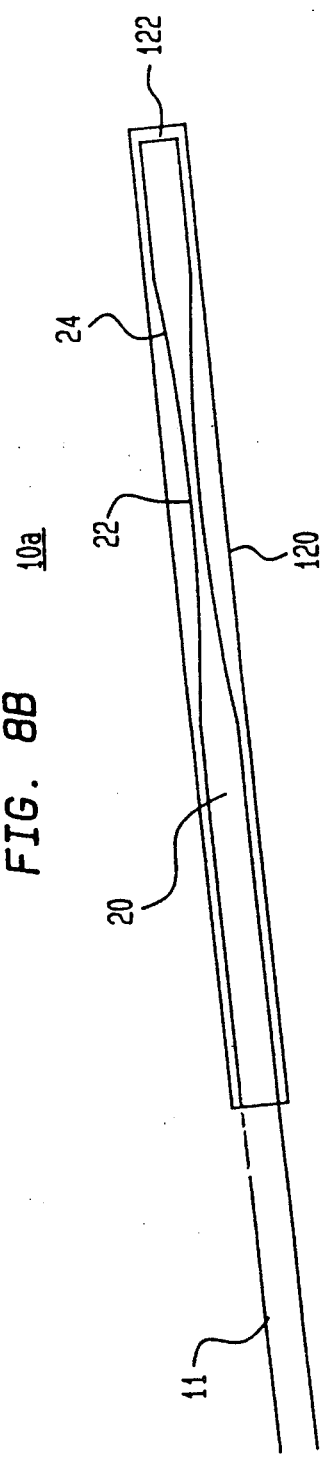

Referring now to FIGS. 8a, 8b, there are shown optical fiber refractometer measurement system 118 and optical fiber refractometer system 10a within optical fiber refractometer measurement system 118. Optical fiber refractometer system 10a is an alternate embodiment of optical fiber refractometer system 10. In optical fiber refractometer system 10a, optical fiber 11 is provided with a tapered region 20, a narrow region 22 and a tapered region 24 as previously described. Additionally, optical fiber 11 is provided with rigid sheath 120 surrounding regions 20, 22, 24. Rigid sheath 120 is provided with perforations to permit liquid to flow through rigid sheath 120 into the interior of rigid sheath 120. Additionally, optical fiber refractometer 20 system 10a is provided with reflector 122 at the end of optical fiber 122 for reflecting light within optical fiber 11. Using optical fiber refractometer system 10a, it is possible to provide a single ended refractometer such as refractometer measurement system 118. In refractometer measurement system 118, reflective end 122 allows all of the light generation and detection to be accomplished at one of end of optical fiber 11.

In optical fiber refractometer measurement system 118, light is launched into optical fiber 11 from LED 124. Light is transmitted from LED 124 through coupler 126 and through optical system 10a which may be immersed in a liquid for measuring the index of refraction of a liquid 14. Some of the light from LED 124 is split-off by coupler 126 and is transmitted to normalizing detector 128. Light is reflected at reflective end 122 and is transmitted back through optical fiber 11 to optical fiber coupler 126. Optical fiber coupler 126 couples reflected light in optical fiber 11 to optical fiber 130 where light may be detected by index reading detector 132. These readings are used to determine the index of refraction of the liquid 14 in which optical fiber refractometer system 10a is immersed in the manner previously described with respect to system 70.

Those skilled in the art will appreciate without any further explanation that many modifications and variations are possible to the above disclosed optical fiber refractometer embodiments, within the concept of this invention. Consequently, it should be understood that all such modifications and variations fall within the scope of the following claims.

What we claim is:

1. A method for measuring the index of refraction of a liquid with an optical fiber refractometer having a light transmitting optical fiber with a fiber axis, comprising;

immersing a portion of said optical fiber in said liquid, launching light into a first end of said optical fiber at a selected non-zero launch angle with respect to said fiber axis, detecting transmitted light at a second end of said optical fiber, and determining the index of refraction of said liquid in accordance with said detected light and said selected non-zero launch angle.

2. The method for measuring the index of refraction of claim 1 wherein the immersed portion of the optical fiber is provided with a tapered region.

3. The method for measuring the index of refraction of a liquid of claim 2 wherein said tapered region is disposed between a reflective end of said optical fiber and means for launching said light.

4. An optical fiber refractometer having a light transmitting optical fiber with a fiber axis and cladding surrounding a fiber core for measuring the index of refraction of a liquid, comprising:

means for immersing a portion of said optical fiber in said liquid, means for launching light into a first end of said optical fiber at a selected non-zero launch angle with respect to said optical fiber axis, means for detecting transmitted light at a second end of said optical fiber, and means for determining the index of refraction of said liquid in accordance with the detected light and the selected non-zero launch angle.

5. The optical fiber refractometer of claim 4, wherein the immersed portion of said optical fiber is provided with a tapered region.

6. The optical fiber refractometer of claim 5, wherein said tapered region is disposed between a reflective end of said optical fiber and said means for launching light.

* * * * *